(12) United States Patent
Bishel

(10) Patent No.: US 9,856,128 B2
(45) Date of Patent: Jan. 2, 2018

(54) MOTORIZED LIQUID DISPENSER

(71) Applicant: Richard A. Bishel, Beaverton, OR (US)

(72) Inventor: Richard A. Bishel, Beaverton, OR (US)

(73) Assignee: Richard A. Bishel, Beaverton, OR (US)

( * ) Notice: Subject to any disclaimer, the term of this patent is extended or adjusted under 35 U.S.C. 154(b) by 0 days.

(21) Appl. No.: 14/397,089

(22) PCT Filed: Apr. 25, 2013

(86) PCT No.: PCT/US2013/038297
§ 371 (c)(1),
(2) Date: Oct. 24, 2014

(87) PCT Pub. No.: WO2013/163482
PCT Pub. Date: Oct. 31, 2013

(65) Prior Publication Data
US 2015/0108169 A1    Apr. 23, 2015

Related U.S. Application Data

(60) Provisional application No. 61/687,530, filed on Apr. 25, 2012.

(51) Int. Cl.
*B67D 3/00* (2006.01)
*A47G 23/02* (2006.01)
*G01F 13/00* (2006.01)
*G01N 33/14* (2006.01)

(52) U.S. Cl.
CPC ....... *B67D 3/0051* (2013.01); *A47G 23/0241* (2013.01); *G01F 13/006* (2013.01); *G01N 33/146* (2013.01)

(58) Field of Classification Search
CPC . B67D 3/0051; A47G 23/0241; G01F 13/006; G01N 33/146
See application file for complete search history.

(56) References Cited

U.S. PATENT DOCUMENTS

| 370,607 A | 9/1887 | Chandler |
| 1,887,881 A | 11/1932 | Blattner |
| 3,170,597 A * | 2/1965 | Reichenberger ..... B67D 3/0051 222/30 |
| 3,868,047 A | 2/1975 | Bersano |

(Continued)

*Primary Examiner* — Frederick C Nicolas
*Assistant Examiner* — Bob Zadeh
(74) *Attorney, Agent, or Firm* — Richard A Bishel

(57) ABSTRACT

A beverage dispenser comprises a bottle holder, a motor, and a controller. The bottle holder is configured to hold a bottle of a liquid beverage. The motor is connected to the bottle holder to cause the bottle holder to tilt. The controller is configured to control the bottle holder via the motor to experience multiple tilting movements, including multiple tilting movements each causing the bottle to tilt by a predetermined angular amount to bring the bottle into a pouring position to dispense a portion of the liquid beverage from the bottle into a serving receptacle. The liquid beverage may be wine, and the serving receptacle may be a wine glass. The liquid beverage may be liquor, and the serving receptacle may be a shot glass. The portion of the liquid may be an amount of liquid to fill the receptacle to a designated level.

20 Claims, 20 Drawing Sheets

(56) References Cited

U.S. PATENT DOCUMENTS

| | | | |
|---|---|---|---|
| 4,317,751 A | 3/1982 | Bishop | |
| 4,473,174 A | 9/1984 | Heuser | |
| 4,624,391 A | 11/1986 | Shannon | |
| 4,702,396 A | 10/1987 | Gwiazda | |
| 4,836,476 A | 6/1989 | Wolf | |
| 4,856,680 A | 8/1989 | Sitton | |
| 4,984,711 A | 1/1991 | Ellis | |
| 5,139,179 A | 8/1992 | Cecil | |
| 5,255,819 A * | 10/1993 | Peckels | B67D 3/0041 222/1 |
| 5,259,238 A * | 11/1993 | Miura | G01N 11/04 73/54.11 |
| 5,335,705 A * | 8/1994 | Morishita | B67D 1/04 141/104 |
| 5,439,142 A | 8/1995 | Robertson et al. | |
| 5,505,349 A * | 4/1996 | Peckels | B67D 3/0041 222/36 |
| 5,507,411 A * | 4/1996 | Peckels | B67D 3/0041 222/1 |
| 5,542,004 A * | 7/1996 | Constant | G01N 33/146 382/100 |
| 5,731,981 A | 3/1998 | Simard | |
| 6,036,055 A * | 3/2000 | Mogadam | B67D 3/0006 222/1 |
| 6,386,393 B1 | 5/2002 | Paulovich et al. | |
| 6,425,421 B1 | 7/2002 | Morrison | |
| 6,568,660 B1 | 5/2003 | Flanbaum | |
| 6,575,337 B1 | 6/2003 | Malavear | |
| 6,889,945 B2 | 5/2005 | McCall | |
| 7,196,624 B2 * | 3/2007 | Teller | B67D 1/1405 222/23 |
| 7,393,112 B1 | 7/2008 | Zell | |
| 7,577,498 B2 | 8/2009 | Jennings et al. | |
| 7,708,241 B2 * | 5/2010 | Wiemholt | A47G 23/0241 222/166 |
| 7,975,881 B1 | 7/2011 | Glucksman et al. | |
| 7,984,813 B1 | 7/2011 | Tapager | |
| 8,011,622 B1 | 9/2011 | Guthrie | |
| 8,033,431 B2 * | 10/2011 | Sommerfield | B67D 1/0412 222/129 |
| 8,496,139 B2 * | 7/2013 | Nishino | B67D 1/04 222/113 |
| 9,022,257 B2 * | 5/2015 | Keating | B67D 3/0003 222/207 |
| 2002/0104583 A1 * | 8/2002 | Andersson | G01N 30/80 141/145 |
| 2002/0139176 A1 * | 10/2002 | Yasui | G01N 33/146 73/60.11 |
| 2003/0213814 A1 * | 11/2003 | Phelps | B01D 53/0446 222/146.6 |
| 2005/0029298 A1 | 2/2005 | Sun | |
| 2005/0103804 A1 | 5/2005 | Waters | |
| 2005/0150549 A1 | 7/2005 | Gosi et al. | |
| 2007/0210109 A1 * | 9/2007 | Wiemholt | A47G 23/0241 222/166 |
| 2007/0217951 A1 * | 9/2007 | Matsumoto | B01F 11/0002 422/67 |
| 2008/0133150 A1 * | 6/2008 | Mogadam | B67D 1/00 702/45 |
| 2008/0195251 A1 * | 8/2008 | Milner | B67D 3/0035 700/237 |
| 2009/0218194 A1 * | 9/2009 | Menke | B65G 17/48 198/404 |
| 2009/0230157 A1 * | 9/2009 | Lindberg | B67D 3/0041 222/504 |
| 2009/0261121 A1 | 10/2009 | Varga | |
| 2010/0155419 A1 * | 6/2010 | Nishino | B67D 1/04 222/81 |
| 2011/0180563 A1 * | 7/2011 | Fitchett | B67D 3/0051 222/1 |
| 2012/0248149 A1 | 10/2012 | Pelfrey | |
| 2012/0272831 A1 | 11/2012 | Barberio et al. | |
| 2013/0119085 A1 * | 5/2013 | Nishino | B67D 1/04 222/91 |
| 2015/0108169 A1 * | 4/2015 | Bishel | B67D 3/0051 222/166 |

* cited by examiner

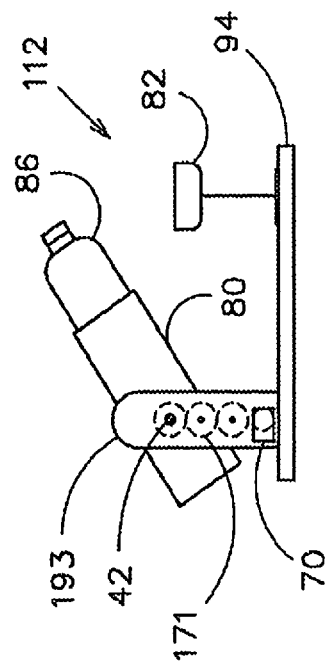
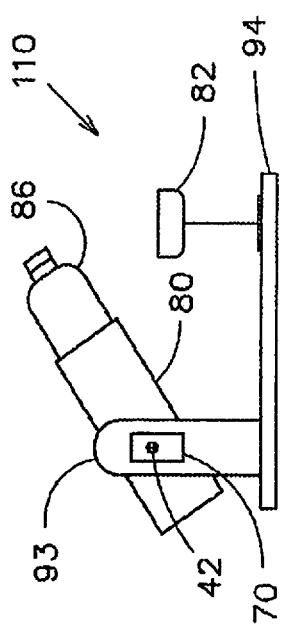
FIG. 7B
FIG. 7A

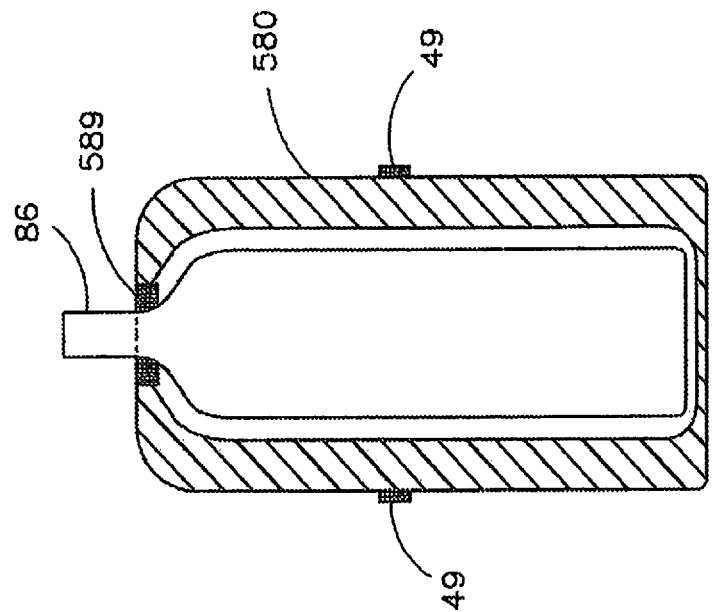
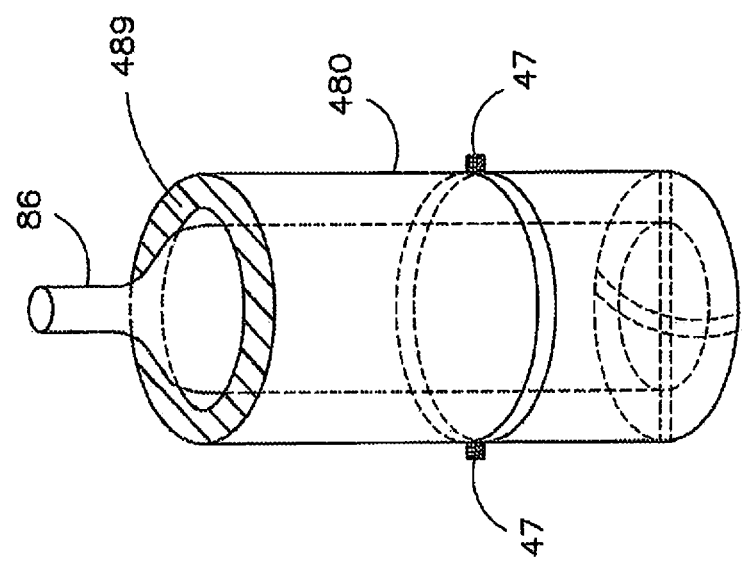
FIG. 12C
FIG. 12D

MOTORIZED LIQUID DISPENSER

RELATED APPLICATIONS

This application is a national stage patent application under 35 U.S.C. §371 of International Patent Application No. PCT/US2013/038297, filed Apr. 25, 2013, and entitled "Motorized Liquid Dispenser," which claims priority to U.S. provisional patent application No. 61/687,530, filed Apr. 25, 2012, entitled "Motorized Liquid Dispenser." Both of the foregoing patent applications are herein incorporated by reference in their entireties.

TECHNICAL FIELD

This disclosure relates generally to automatically or semi-automatically dispensing liquid from one container to another. More particularly, this disclosure related to an apparatus for automatically or semi-automatically dispensing a serving of a beverage from a container to a serving receptacle using an electric motor.

BACKGROUND INFORMATION

Pivotable supports have been used for many years to facilitate dispensing liquid from containers, from very small bottles of wine and distilled liquors as disclosed in U.S. Pat. No. 3,868,047 by Bersano, to large barrels of gasoline or oil as disclosed in U.S. Pat. No. 1,755,745 by Parr.

Prior art in dispensing small bottles is in the area for decanting of wines such as the manual process using a hand crank and pulleys, gears, or friction as disclosed in U.S. Pat. No. 3,868,047 by Bersano, or serving wines using a knob on the pivotal device disclosed in U.S. Pat. No. 6,889,945B2 by McCall. Both methods rely on the individual or server to pour the proper portion of liquid into the glass or container. Wiemholt discloses in U.S. Pat. No. 7,708,241 B2 automating the wine decanting process using a tilting process where the entire bottle is dispensed into a container.

There is also prior art using pumps such as disclosed in U.S. Pat. No. 6,435,421 issued to Morrison, or pressurized gas disclosed in U.S. Pat. No. 5,139,179 by Cecil. Additionally, there are many gravity-fed systems, where the bottle is placed upside down with the opening on the bottom and a manual valve controls the liquid. Automating the process is disclosed in U.S. Pat. No. 3,930,598 by Slagle.

SUMMARY OF THE DISCLOSURE

This disclosure relates to an apparatus for dispensing liquid from one container to another automatically. The liquid may be a consumable beverage, such as, for example, wine, water, juice, milk, beer, nectar, syrup, honey, soda, liquor, or the like, or mixtures of the foregoing.

According to one embodiment, a beverage dispenser comprises a bottle holder, a motor, and a controller. The bottle holder is configured to hold a bottle of a liquid beverage. The motor is connected to the bottle holder and configured to move the bottle holder in an angular movement to bring the bottle into a pouring position. The controller is configured to control the bottle holder via the motor in a set pattern to dispense a portion of the liquid beverage from the bottle into a serving receptacle.

Some optional aspects of this embodiment include the following. The liquid beverage may be wine, and the serving receptacle may be a wine glass. The liquid beverage may be liquor, and the serving receptacle may be a shot glass. The bottle holder may be a container, which may be insulated. Alternatively, the bottle holder may be a wired cage. The motor be an electric motor. The controller may be selected from the group consisting of, for example, a computer, a microcontroller, and control circuitry. The set pattern may comprise angular positions of the bottle holder over time. The portion of the liquid may be an amount of liquid to fill the receptacle to a designated level. The portion of the liquid beverage is less than the entire capacity of the bottle. The beverage dispenser may further comprise a temperature sensor configured to monitor the temperature of the bottle.

Optionally, the beverage dispenser may further comprise a sensor configured to detect presence of the receptacle in a position to accept the beverage poured from the bottle, and the controller may be further configured to dispense a portion of the beverage from the bottle into the receptacle when the receptacle is detected via the sensor. The sensor may be selected from a group consisting of, for example, a weight sensor, a switch, a photo detector sensor, a motion sensor, a distance sensor, and a force sensor.

Optionally, the beverage dispenser may further comprise a wireless receiver configured to accept signals from a remote device, and the controller may be connected to the wireless receiver to accept a command from the remote device. The remote device may be selected from a group consisting of, for example, a handheld computer, a tablet, or a smart phone. The command may be a command to dispense a serving of the beverage into the serving receptacle.

Optionally, the beverage dispenser may further comprise a movable platform having a plurality of positions for a respective plurality of serving receptacles, and a motor connected to the movable platform and configured to move the movable platform to position each of the plurality of serving receptacles into a position to accept the a portion of the beverage poured from the bottle. The controller may be connected to the motor and further configured to move the movable platform to position each of the plurality of serving receptacles into a position to accept a portion of the beverage poured from the bottle. The movable platform may be a turntable.

According to another embodiment, a method comprises mechanically accepting and holding a bottle containing a beverage, and automatically or semi-automatically moving the bottle in an angular movement from a first position to a second position, wherein the first position is a position maintaining the beverage within the bottle, and the second position is a pouring position to cause a portion of the beverage to pour into a serving receptacle.

Optionally, the beverage may be wine, and the serving receptacle may be a wine glass. Alternatively, the beverage may be liquor, and the serving receptacle may be a shot glass. The step of moving the bottle may comprise moving the bottle by a predetermined angle over a predetermined time. The portion of the beverage may be an amount to fill the serving receptacle to a designated level. The method may further comprise sensing presence of the receptacle in a position to accept the beverage poured from the bottle, and the moving step may be performed in response to sensing presence of the receptacle in a position to accept the beverage poured from the bottle. The method may further comprise receiving a wireless signal from a remote device, and the moving step may be performed in response to receipt of the wireless signal. The remote device may be selected from a group consisting of, for example, a handheld computer, a tablet, or a smart phone. The method may further comprise monitoring the temperature of the bottle. The method may further comprise automatically or semi-automatically moving a plurality of serving receptacles into position to accept a portion of the beverage poured from the bottle. The portion of the beverage is less than the entire capacity of the bottle.

According to yet another embodiment, a beverage pouring apparatus comprises means for accepting and holding a bottle containing a beverage, and means for at least semi-automatically moving the bottle in an angular movement from a first position to a second position, wherein the first position is a position maintaining the beverage within the bottle, and the second position is a pouring position to cause a portion of the beverage to pour into a serving receptacle. The means for accepting and holding a bottle containing a beverage may comprise a container, frame, or any other mechanism. The means for at least semi-automatically moving the bottle may comprise an electric or non-electric motor in combination with a controller, such as computer, microcontroller, or circuitry.

BRIEF DESCRIPTION OF THE DRAWINGS

FIG. 7A is a side view of another embodiment of the apparatus with brackets holding the container.

FIG. 7B is a side view of another embodiment of the apparatus with gears moving the container.

FIG. 12C is an isometric view of the container of the apparatus consisting of wired cage.

FIG. 12D is a top view of the container made as cradle.

DETAILED DESCRIPTION OF EMBODIMENTS

Figure 1:
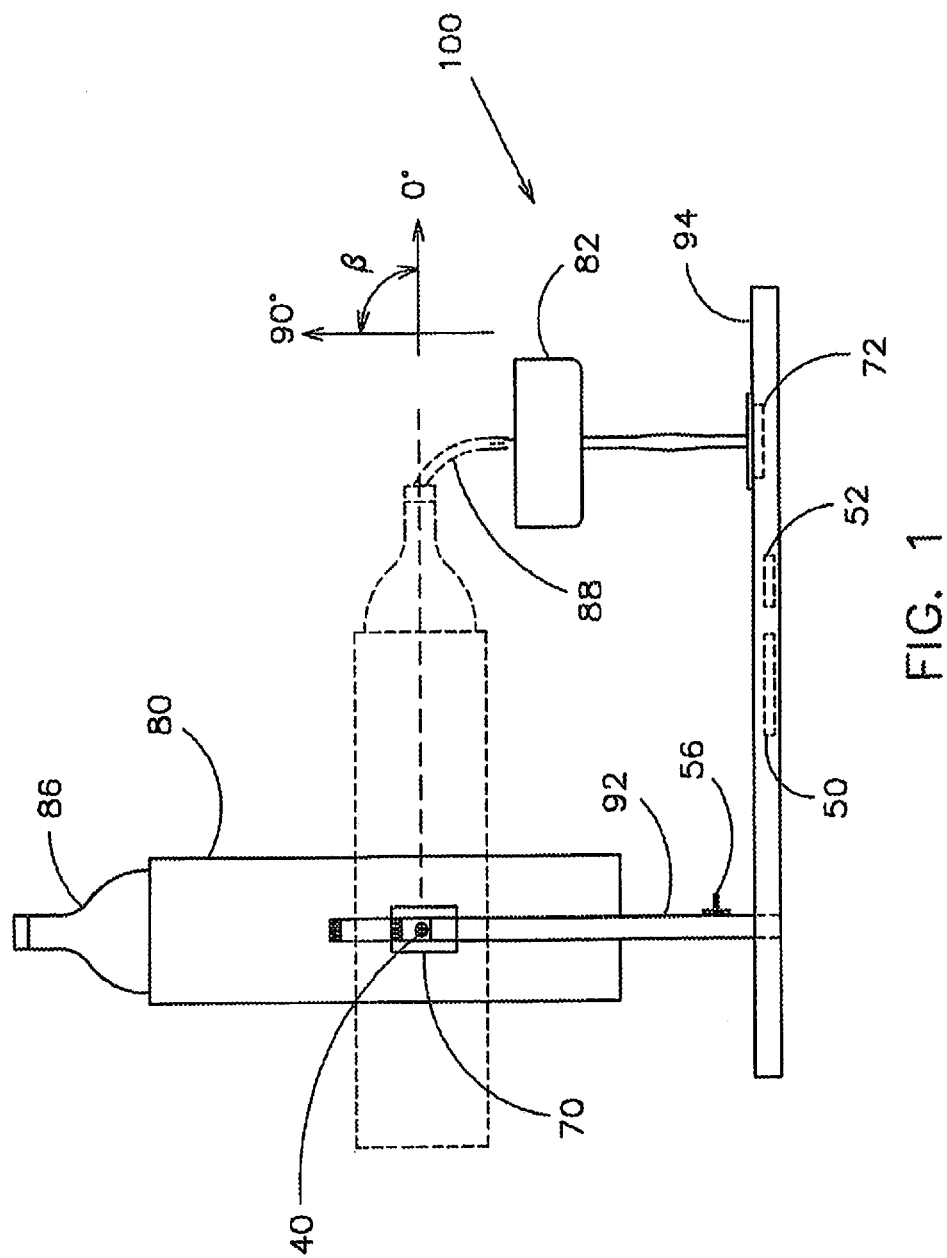
FIG. 1 is a side view of one embodiment of the apparatus showing the pouring action.

With reference to the above-listed drawings, this section describes particular embodiments and their detailed construction and operation. The embodiments described herein are set forth by way of illustration only and not limitation. Those skilled in the art will recognize in light of the teachings herein that there are alternatives, variations and equivalents to the example embodiments described herein. For example, other embodiments are readily possible, variations can be made to the embodiments described herein, and there may be equivalents to the components, parts, or steps that make up the described embodiments.

For the sake of clarity and conciseness, certain aspects of components or steps of certain embodiments are presented without undue detail where such detail would be apparent to those skilled in the art in light of the teachings herein and/or where such detail would obfuscate an understanding of more pertinent aspects of the embodiments.

As one skilled in the art will appreciate in view of the teachings herein, certain embodiments may be capable of achieving certain advantages, including by way of example and not limitation one or more of the following: (1) Providing restaurants, bars, cocktail lounge businesses, and the like a device to automate the process to provide a proper portion of liquid to be poured without error from the servers and without pumps or turning bottles upside down; and (2) providing elderly, infirm, weak, handicapped, or incapacitated individuals a device for pouring a portion of a liquid from containers, especially larger containers such as half or full gallons of milk. These and other advantages of various embodiments will be apparent upon reading the following.

Before proceeding with a detailed description of the illustrated embodiments, the following is provided as an overview.

A liquid dispenser having a receptacle or other holder for a bottle of liquid can rotate the receptacle. The receptacle may be connected to a motor, which may be electric, so that the motor can rotate the receptacle and therefore, the bottle of liquid. A controller may be programmed or otherwise configured to control the motor in a set sequence or pattern to dispense a portion of the liquid from the bottle. The bottle may be rotated to pour the liquid into a glass or other container. Furthermore, the sequence can be initiated via a sensor which detects the presence of the glass.

The motorized liquid dispenser contains a first container for holding the bottle of liquid and the motor may be connected to the first container to rotate or move the first container in an angular movement to bring the bottle from one position to a substantially different position to enable pouring of the liquid from the bottle. Furthermore, a controller may be programmed or otherwise configured to control the motor and in turn controls the angular position of the first container in a set pattern or sequence to dispense a portion of the liquid from the bottle in the first container to a second container such as a glass or cup. Furthermore, the initiation of this sequence may be from a sensor detecting the second container when place on the apparatus.

The dispenser is well suited for an automated dispensation of wine using a container to hold the wine bottle. An electric motor may be connected to the container to move the container and therefore the wine bottle in an angular motion to a pouring position. A controller may be programmed or otherwise configured to control the electric motor in a set pattern to dispense a portion of the wine in the bottle to the glass. Furthermore, the initiation of the sequence may be from a sensor that detects the glass placement.

Referring to the drawings, wherein like referenced numerals represent like parts throughout the various drawing figures, reference numeral 80 is directed to the container for holding the bottle.

Figure 2:
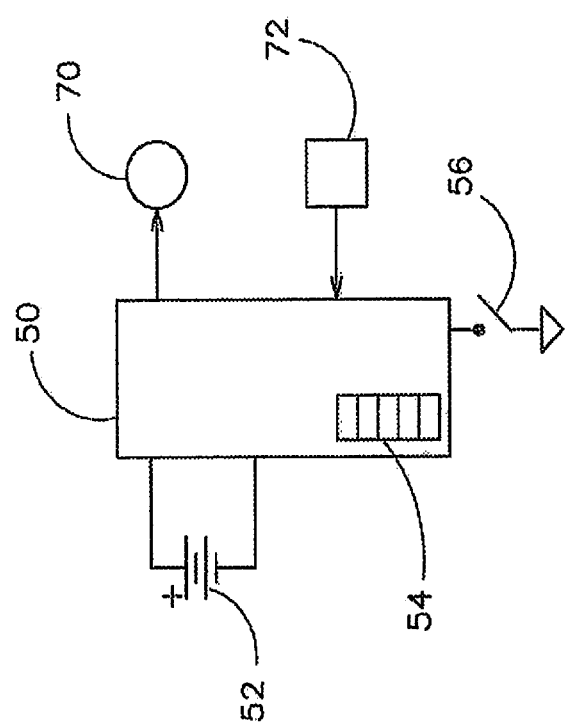
FIG. 2 is a block diagram of a controller circuit.

FIG. 1 shows one embodiment 100 which dispenses a portion of the liquid into bottle 86 to the glass 82 automatically as soon glass 82 is placed on the sensor 72. In particular, the bottle 86 of liquid is placed in the container 80. The bottle 86 may be held in place by the friction of the inside of the container or bottle holder 80 or sleeve (not shown) on the bottle 86. An electric motor 70, in particular, a servo motor, a hobby servo motor, a position-controlled motor, a stepper motor, or a motor-controlled system, controls an angular position beta, $\beta$, and an angular rate of change of the container 80 about the pivot point 40 on the vertical rods 92 (not shown is the second rod on the opposite side). The vertical rods 92 are supported by a base 94. Inside the base 94 is the controller 50 and a power source 52, which may be batteries, re-chargeable batteries, or an attachment to an external power supply. The controller 50, which is shown in FIG. 2 along with the power source 52 in the form of batteries and an on/off switch 56, takes input from the glass sensor 72, which detects the glass 82 when placed on the base 94 and controls the electric motor 70 according to a stored profile 54 in FIG. 3. The glass sensor 72 may be, for example, a weight sensor, a switch, a photodetector sensor, a motion sensor, a distance sensor, or a force sensor. The controller 50 can be, for example, a microcontroller, a small computer, or dedicated control circuitry. The stored profile 54 contains the angular positions beta $\beta$ at various time intervals.

Figure 3:
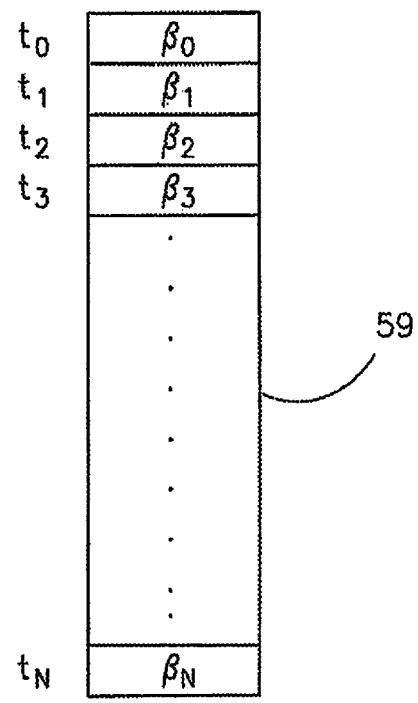
FIG. 3 is a programmed sequence showing time and corresponding angular positions.

FIG. 3 shows, at time $t_0$, the angular position $\beta_0$ is stored; at time $t_1$, the angular position $\beta_1$ is stored; and so on. This profile continues until the final time $t_N$ and the angular position $\beta_N$ are stored. The stored profile 54 may be derived from a recorded position of a person pouring the liquid from the bottle to the glass. The stored profile is a replica of the recorded position and the controller 50 plays back the profile as if it was the original profile.

Figure 4:
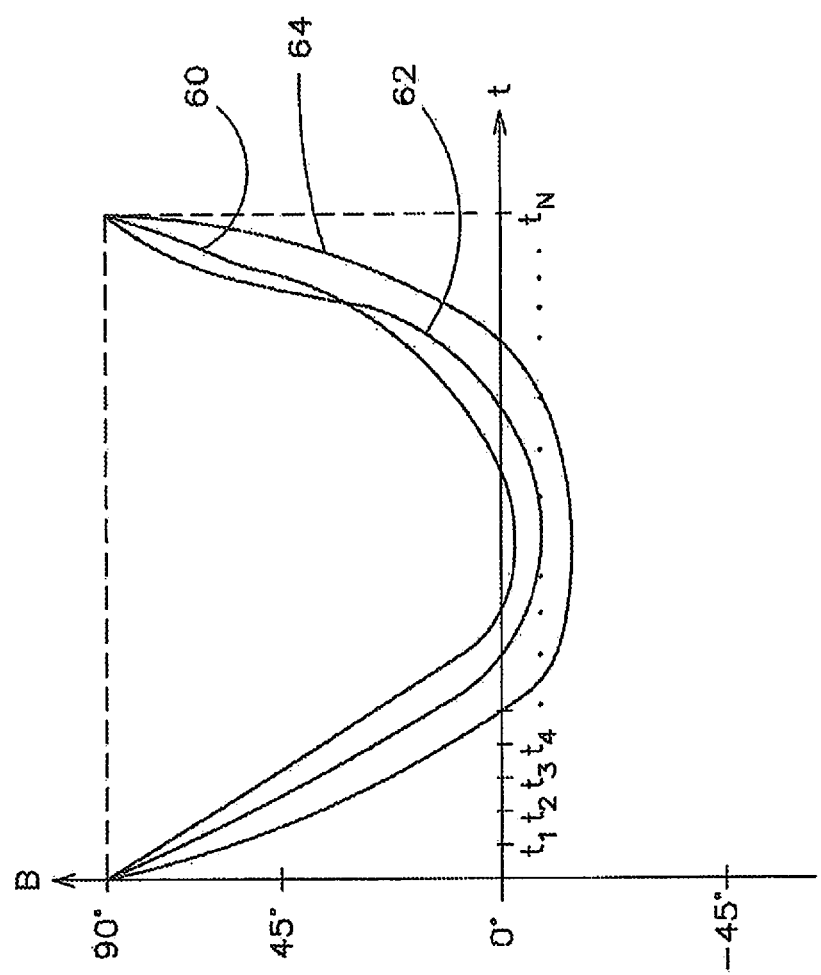
FIG. 4 is a set of graphs of the programmed sequence with angular positions vs. time.

FIG. 4 shows profiles for a particular bottle 86 being poured into several glasses. Profile 60 represents the recording of the first time the bottle 86 is poured into the glass 82. Profile 62 is the next pour for the second glass, profile 64 would be the third glass, and so on. As shown in FIG. 4, the container 80, and therefore the bottle 86 is in an upright position (vertical position), $\beta=90$ degrees referring to the small graph in FIG. 1. While the liquid is dispensing into the glass 82, the container 80 and the bottle 86 are near or below horizontal position, $\beta=0$ degrees or less to disperse the liquid from the bottle 86. After pouring a portion of the liquid from the bottle 86, the container 80 and bottle return to the vertical position, $\beta=90$ degrees or some other inclined position sufficiently upright to hold the remaining contents of the bottle 86.

Figure 5A:
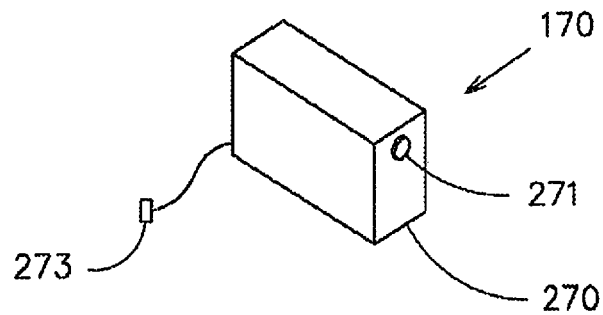
FIG. 5A is an isometric view of a hobby servo motor.
Figure 5B:
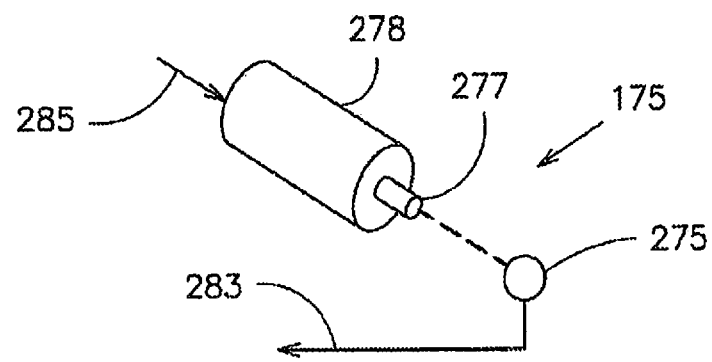
FIG. 5B is an isometric view of a motor control system.
Figure 5C:
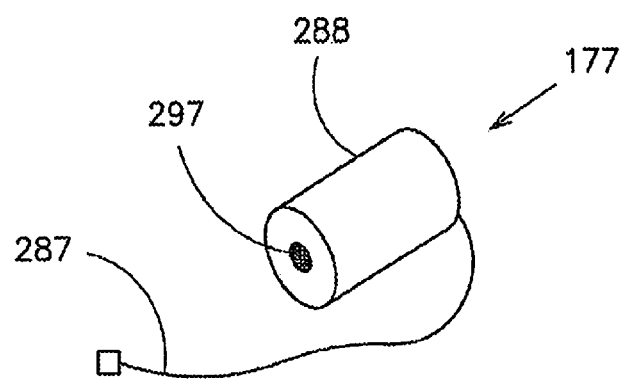
FIG. 5C is an isometric view of a stepper motor.

FIGS. 5A-C show several different types of electric motors that can provide precision pours in combination with the controller 50. FIG. 5A illustrates of one type of motor 170, called a hobby servo motor 270, with an output gear 271, and a 3-pin wire input 273. The wire input provides power, ground, and a command signal. Servo motors of this type provide different torque and speed ratings for different applications. For pouring a glass of wine from a 750 ml wine bottle or portion of the wine from the 750 ml wine bottle in the previously described in FIG. 1, a typical torque rating of 80 oz-in and a speed rating of 0.2 seconds/60 degrees would work fine for a motor 70. For a gallon jug, a higher torque rating would be needed. FIG. 5B illustrates another type of motor 175, called a servo motor controlled system which contains an electric motor 278, a output gear 277, and a feedback sensor 275 such as a potentiometer. The electric motor 278 is driven from a current driver (not shown) via electric connection 285 from the controller. The controller drives the motor output 277 to the proper angular position based off of information from the feedback sensor 275. FIG. 5C illustrates another type of motor 177 called a stepper motor 288, which requires a starting position and counts. The controller keeps track of the steps in the stepper motor unit. The output gear 297 would drive the angular motion, and the drive capability for the stepper motor 288 is from the wired connection 287.

Figure 6B:
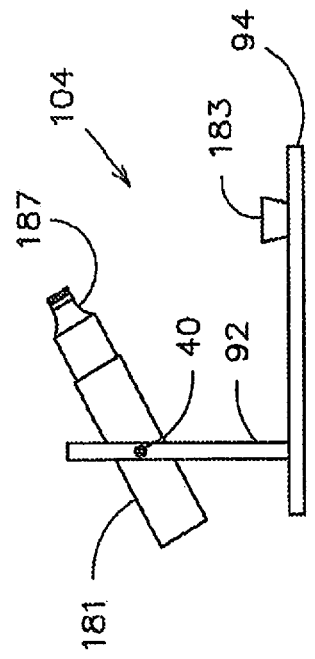
FIG. 6B is a side view of another embodiment of the apparatus with a long bottle.
Figure 6D:
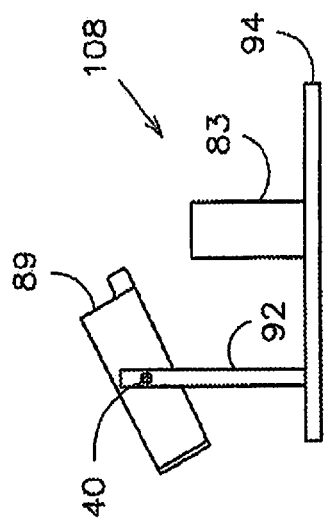
FIG. 6D is a side view of another embodiment of the apparatus with a bottle and container as one unit.
Figure 6A:
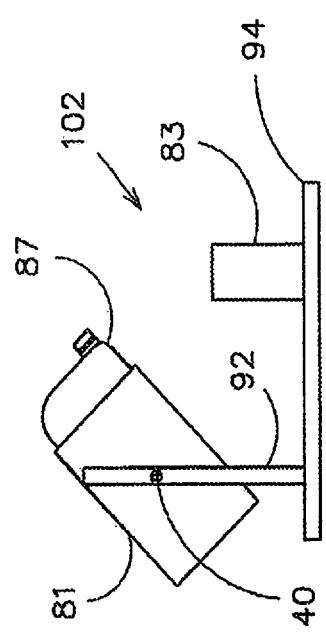
FIG. 6A is a side view of another embodiment of the apparatus with a gallon container.

FIG. 6A-6D show different embodiments for different types of bottles. FIG. 6A illustrates embodiment 102 which dispenses liquid from the gallon jug 87 into a cup 83. The controller and operation is similar to what has been described above but with a different stored profile. FIG. 6A shows the container 81 which holds a gallon container 87 which is controlled at pivot point 40. The vertical rods 92 support the container 87 and the base 94 supports the rods 92 and the cup 83.

FIG. 6B illustrates embodiment 104 in which the container 181 holds a long neck bottle 187. In a similar manner, the vertical rod 92 holds the container about the pivot point 40 along the rod axis. The electric motor (not shown in this figure) controls the angular position of the container 181 to dispense a small portion of the liquid from the bottle 187 into a short glass 183. The precision pour would provide the correct portion of liquid typically used in a bar situation. The operation of dispensing the liquid is similar as described previously, but the stored profile would be different.

Figure 6C:
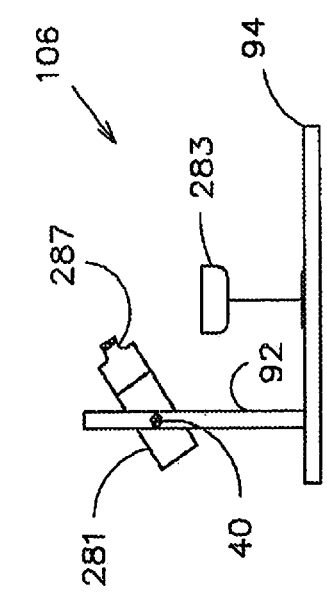
FIG. 6C is a side view of another embodiment of the apparatus with a short bottle.

FIG. 6C illustrates an embodiment 106 holding a short bottle 287 with container 281. The short bottle could be a beverage bottle. FIG. 6D shows the container and bottle 89 as the same unit. In this embodiment 108, one would add the liquid into the container 89 prior to dispensing.

FIG. 7A shows an embodiment 110 having a different mechanical mechanism for holding the container 80. Instead of vertical rods, the container 80 pivots on two support brackets 93 and pivot point 42, one on each side. The embodiment 110 contains the brackets 93 along with the electric motor 70. The bottle 86, glass 82, and base 94 are the same as described previously. FIG. 7B shows the similar bracket 193 as in FIG. 7A but the electric motor 70 is mounted near the base 94 of the embodiment 112. Gears 171, inside the bracket 193, control the container 80 about the pivot point 42 on the top of the bracket 193.

Figure 8:
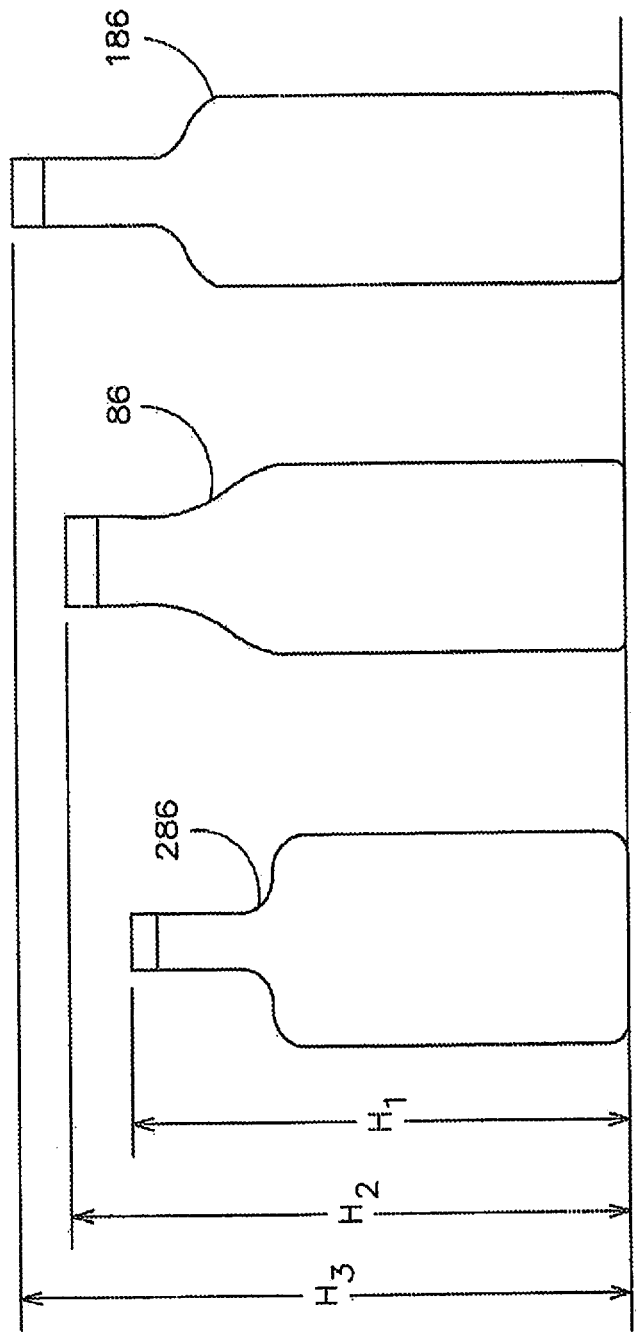
FIG. 8 is a side view of different heights and sizes of bottles.
Figure 9:
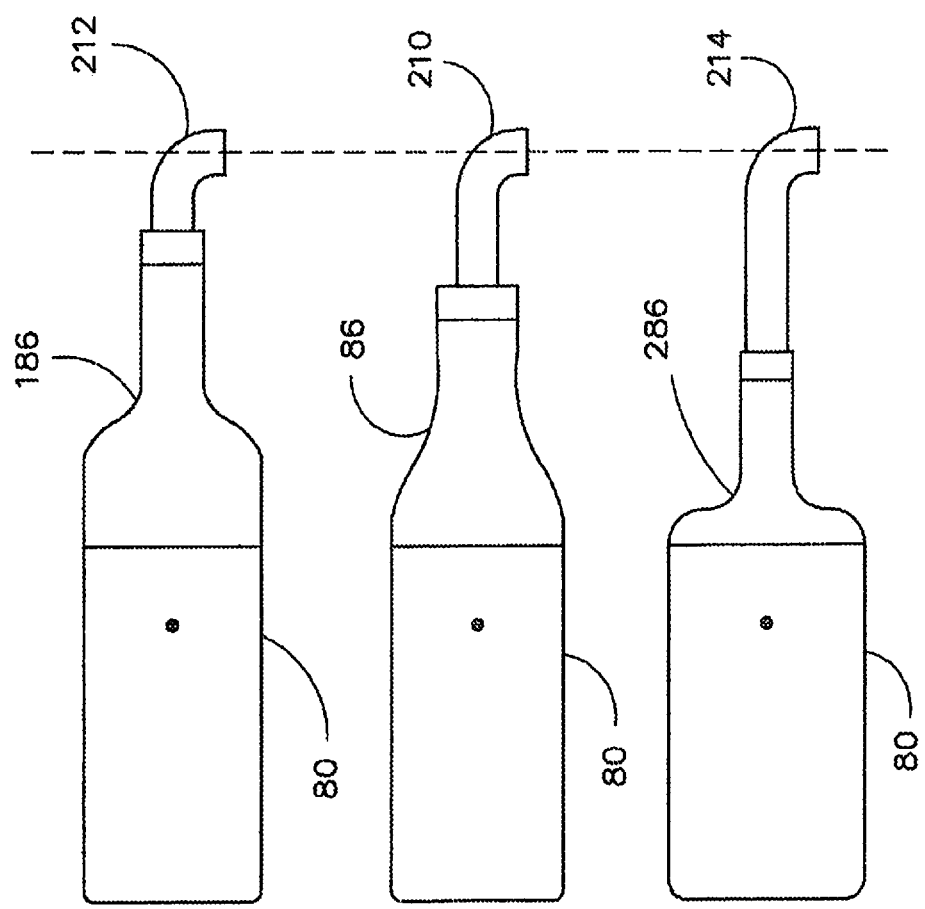
FIG. 9 is a side view of the different bottles with different length pouring spouts attached.

FIG. 8 shows different lengths, H1, H2, and H3, of particular 750 ml wine bottles, 286, 86, and 186, respectively. In order to accommodate these bottles without building a new fixture, the attachment pouring device with different lengths can accommodate the bottle length as shown in FIG. 9. The bottle 286 is the shortest one and uses the longest neck pourer 214. The bottle 186 is the longest and uses the shortest pourer 212. The standard length bottle 86 uses the standard pourer 210.

Figure 10A:
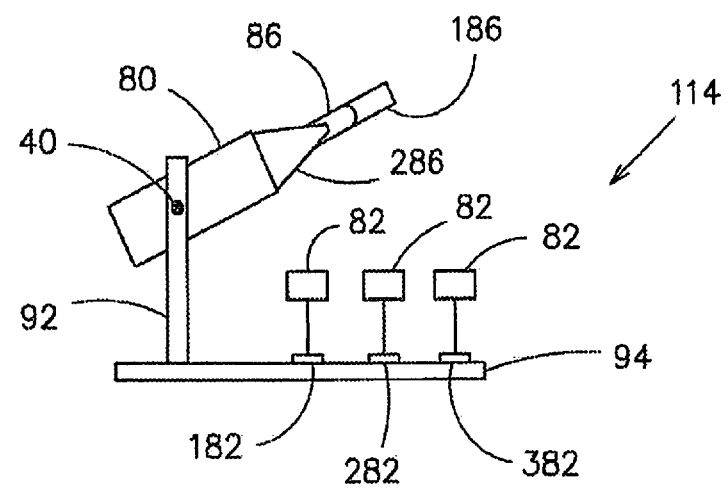
FIG. 10A is a side view of another embodiment of the apparatus showing different placements of the glass.

Another method to accommodate the different length bottles 286, 86, and 186 is by leaving different pads 182, 282, and 382 on the base 94, as shown in FIG. 10A. For short length bottles such as 286, the pad 182 would allow the liquid from the bottle to be dispensed properly by having glass 82 on pad 182. Likewise, bottle 86 would be dispensed properly in same type of glass 82 at pad 282 and bottle 186 would be dispensed properly in similar glass 82 on pad 382 as shown in FIG. 10A.

Figure 10B:
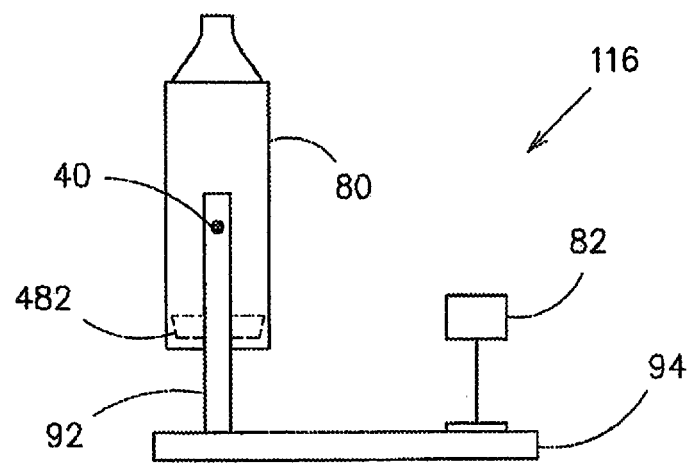
FIG. 10B is a side view of another embodiment of the apparatus illustrating an insert within the container.

Another method to accommodate different length bottles is shown in FIG. 10B, wherein an embodiment 116 shows different inserts 482 that are used to accommodate the different length bottles in the container 80.

Figure 11:
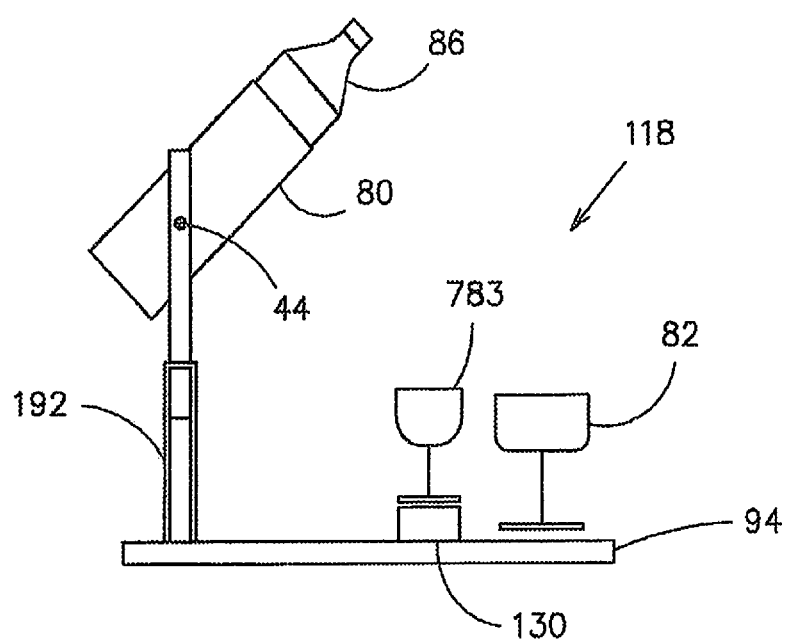
FIG. 11 is a side view of another embodiment of the apparatus illustrating two methods for accommodating the different heights of glasses.

To accommodate different glass heights, embodiment 118 shows two methods in FIG. 11 that can be used. Standard height glass 82 is at proper height for bottle 86 to pour the liquid. To accommodate glass 783, one method would be to raise the glass 783 by an insert 130 on the base 94. Another method would be to raise or lower the vertical rods 192 or axis point 44, also shown in FIG. 11. Note that similar sized glasses within a certain range can be easily accommodated by the proper height of the axis point 44. Beside glasses, one can pour into cups, smaller bottles, serving containers, shot glasses, or flasks.

Figure 12B:
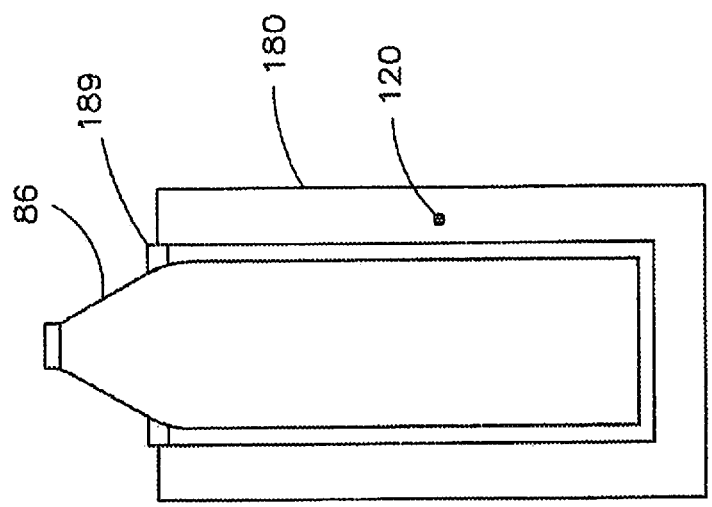
FIG. 12B is a side view of the container of the apparatus with an insulated jacket insert.
Figure 12A:
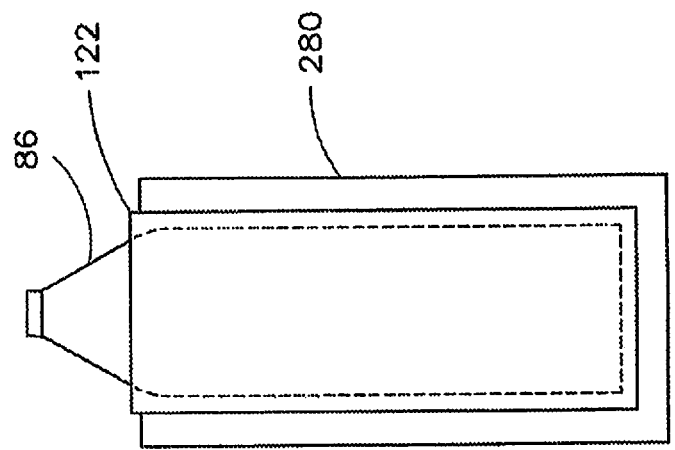
FIG. 12A is a side view of the container of the apparatus with a vacuum.

Since the container would be on a table or counter, the liquid may cool or warm up based on the difference in bottle temperature versus room temperature. To minimize this effect, in the embodiments 100-118, the container may contain a vacuum similar to thermos bottles or an insulated jacket. In FIG. 12A shows a container 180 containing a vacuum 120 to keep the temperature of the bottle 86 from changing quickly. FIG. 12B shows container 280 with an insulated material 122. FIG. 12C shows an isometric view of the container 480 made from a thick wired cage. The bottle 86 is placed within the wired cage 480 and a rubber or flexible material ring 489 secures the bottle 86 with the wired cage 480. The pivot points 47 are shown on the middle section of the wired cage 480. FIG. 12D shows a top view of the container 580 where the bottle 86 lies in the container like a cradle. A rubber or flexible material secures the bottle 86. The pivot points 49 are shown on the container 580 where the unit is rotated.

Figure 13:
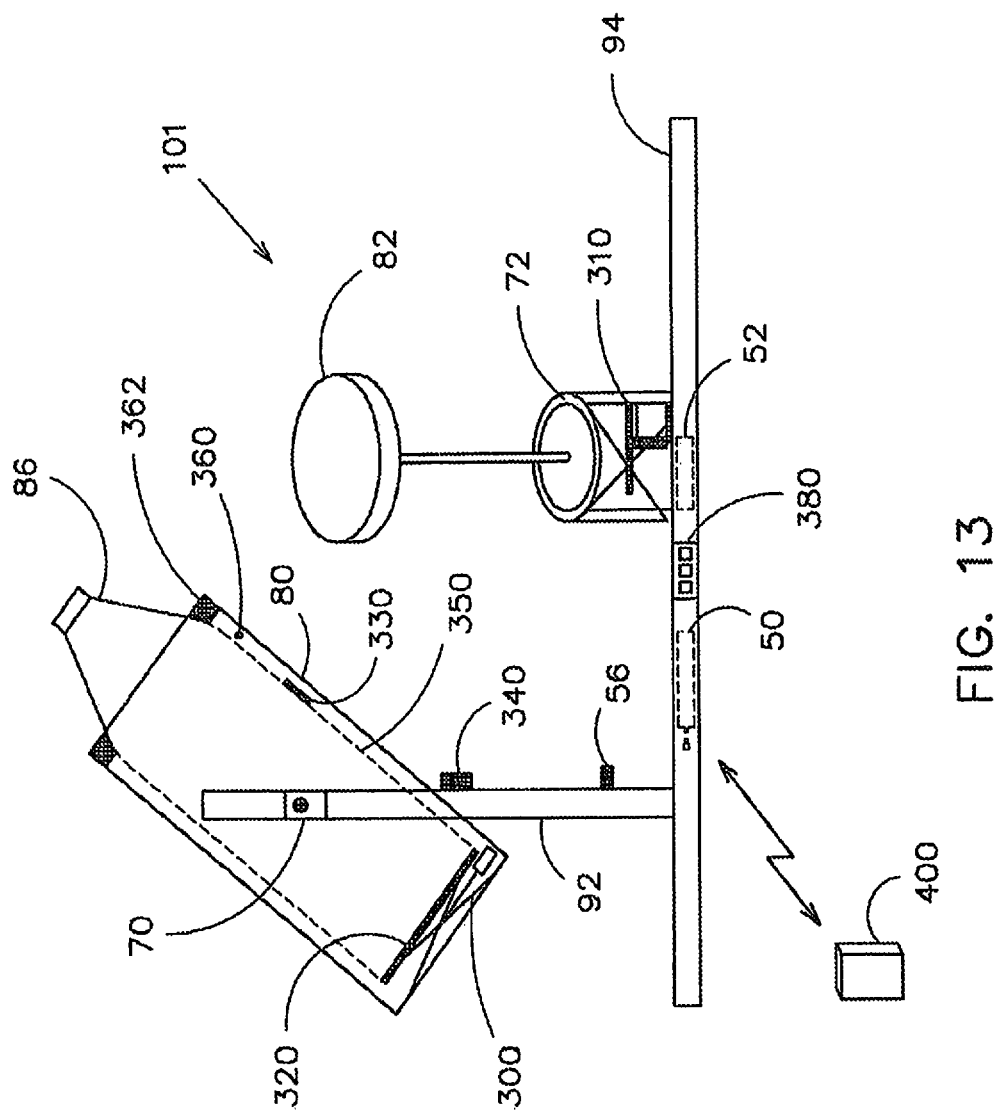
FIG. 13 is a side view of another embodiment of the apparatus illustrating a number of features.
Figure 14:
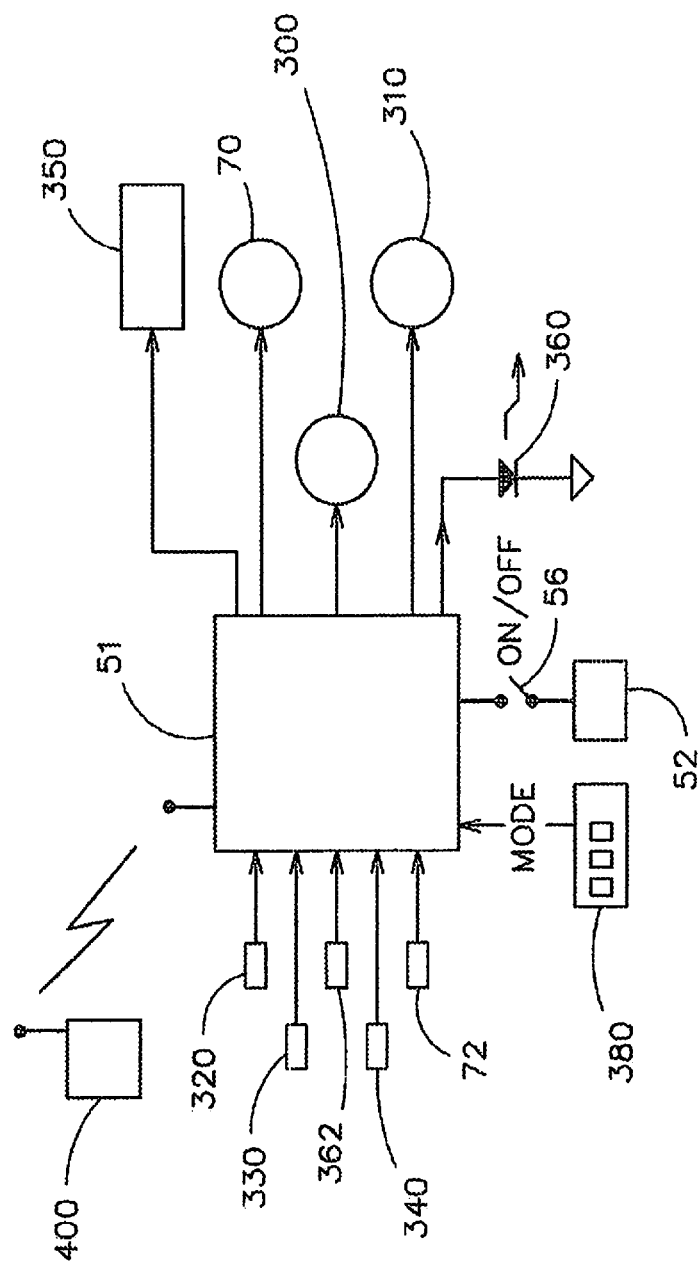
FIG. 14 is a block diagram of a circuit showing a number of attached items.

FIG. 1 shows the basic concept of the embodiment 100. FIG. 13 shows additional features that can be incorporated into an embodiment 101. FIG. 13 shows another method to accommodate the glass 82 height by utilizing a scissor-type mechanism 310 to raise or lower the glass via an electric motor. Likewise, the different length bottles can be accommodated by scissor-type mechanism 300 which raises or lowers the bottle 86. A weight sensor 320 can be used to detect the presence of the bottle 86 and the amount of liquid in the bottle 86. In addition to the glass sensor 72, another method for detecting the glass would be via a distance or object sensor 340. The temperature sensor 330 measures the temperature of the liquid in bottle 86. LEDs 360 may be mounted on the container 80 as shown in FIG. 13 or on the base 94 (not shown) or rod 92 (not shown). A keypad 380 is shown attached to the base 94 and the keypad 380 can select profiles, modes of operation, bottle types, or glass types. Also shown, a remote control device 400 can be a handheld computer, tablet, or smart phone or other smart device for controlling the operation wirelessly or for selecting similar functions as the keypad 380, but remotely. FIG. 14 shows the block diagram of the some of the input and output devices that the controller 51 that can be implemented. Input devices, such as weight sensor 320, temperature sensor 330, bottle detector 362, object sensor 340, glass sensor 72, keypad 380, switch 56, and remote control device 400 are shown in FIG. 14. The output devices can be motor to control the scissor-type mechanism 300, an electric motor 70 to control the angle of the container 80, electric motor to control the scissor-type mechanism 310, an electric heater/cooler element 350, and LEDs 360.

Figure 15:
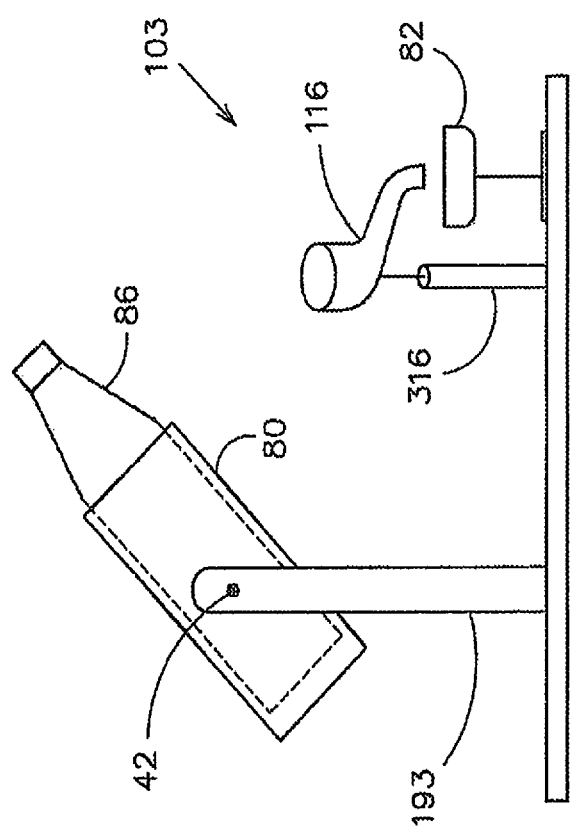
FIG. 15 is a side view of another embodiment of the apparatus using a funnel.

FIG. 15 shows another embodiment 103 which uses an additional funnel 116 to bring the liquid from the bottle when poured via the controller/motor to the glass 82. Different glasses can be accommodated by adjusting the height of the funnel via a mechanism 316.

Figure 16A:
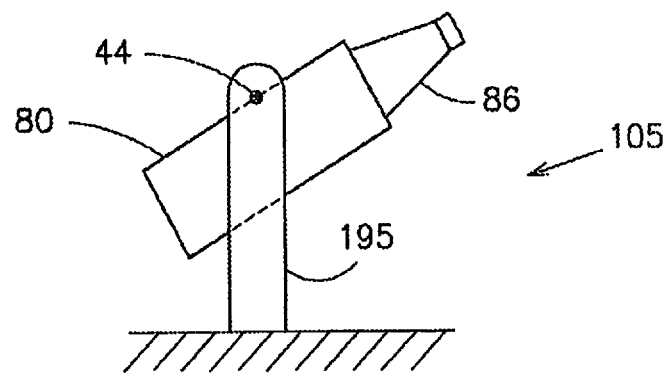
FIG. 16A is a side view of the container mounted at the top of the container.
Figure 16B:
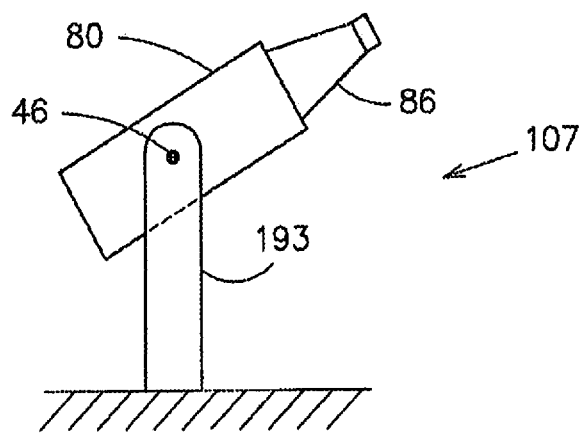
FIG. 16B is a side view of the container mounted at the center of the container.
Figure 16C:
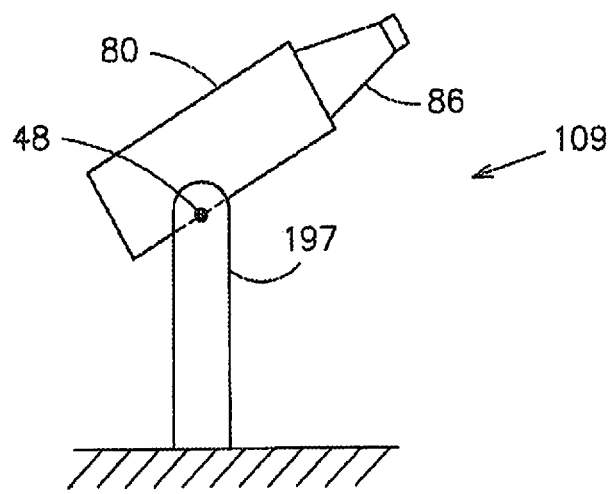
FIG. 16C is a side view of the container mounted at the bottom of the container.
Figure 17:
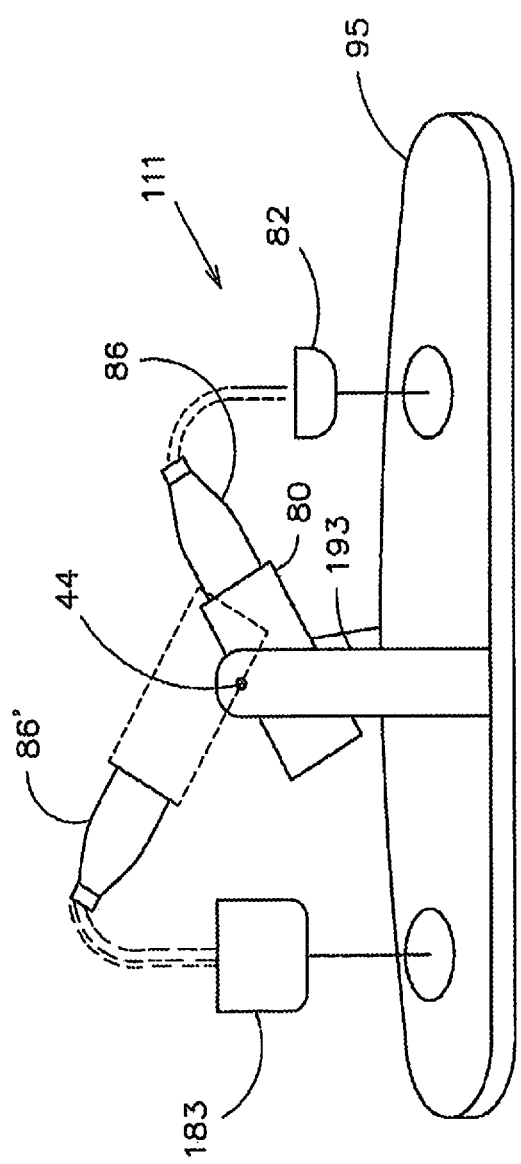
FIG. 17 is a side view of another embodiment of the apparatus that allows for pouring different height glasses.

FIG. 16A-C shows three different embodiments 105, 107, and 109, respectively, for different pivot locations. In FIG. 16A, an embodiment 105 contains a pivot point 44 that is located on top of the container with bracket 195. In FIG. 16B, an embodiment 107 contains a pivot point 46 that is located in the center of the container with bracket 193 as shown previously. In FIG. 16C, an embodiment 109 contains a pivot point 48 that is located on the lower side of the container with bracket 197. Another embodiment 111 shown in FIG. 17 illustrates how the pivot point 44 stays the same but the container 80 rotates from one side to pour the bottle 86 in a shorter glass 82 and on the other side as shown with bottle 86 into a taller glass 183. The base plate 95 would be longer in this embodiment.

Figure 18A:
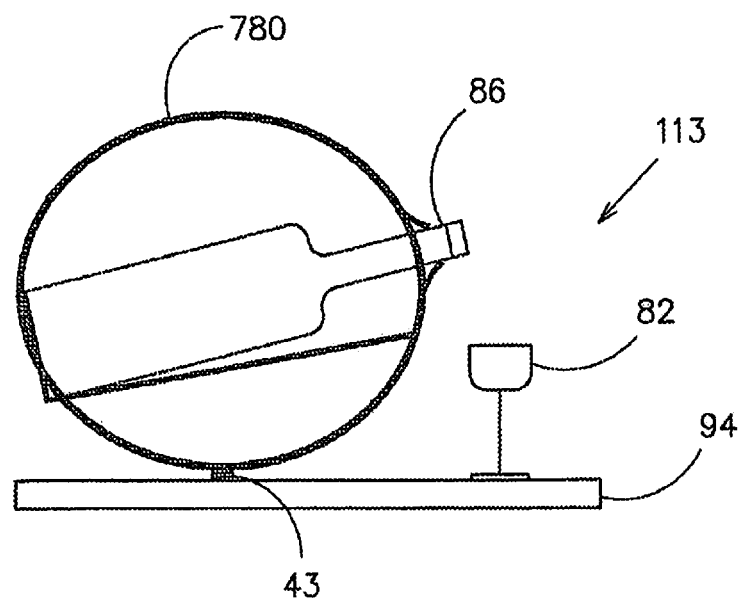
FIG. 18A is a side view of another embodiment of the apparatus that incorporate a wired cage as the container.
Figure 18B:
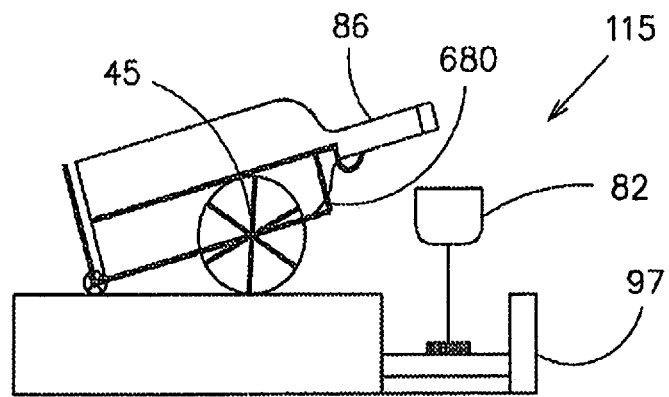
FIG. 18B is a side view of another embodiment of the apparatus that incorporate a wheel-type mechanism as the container to hold the bottle.

FIG. 18A and FIG. 18B shows other embodiments that utilize a different mechanism to hold the bottle instead of the vertical rods or bracket to hold the container. In FIG. 18A, embodiment 113 shows the bottle 86 is being held in a thick wired cage 780 and the pivot point 43 & motor combination is on the base 94 to rotate the wired cage. By rotating the wired cage and bottle, the liquid is poured into the glass 82 similarly as described previously. FIG. 18B shows another embodiment 115 with the pivot point 45 positioned on the wheel carriage 680 which cradles the bottle 86. The base 97 accommodates different glasses such as glass 82 by inserts or scissor-type mechanisms as previously described. In FIG. 18B, the bottle is rotated with the wheel and therefore, the liquid from the bottle 86 is poured into the glass 82.

Figure 19:
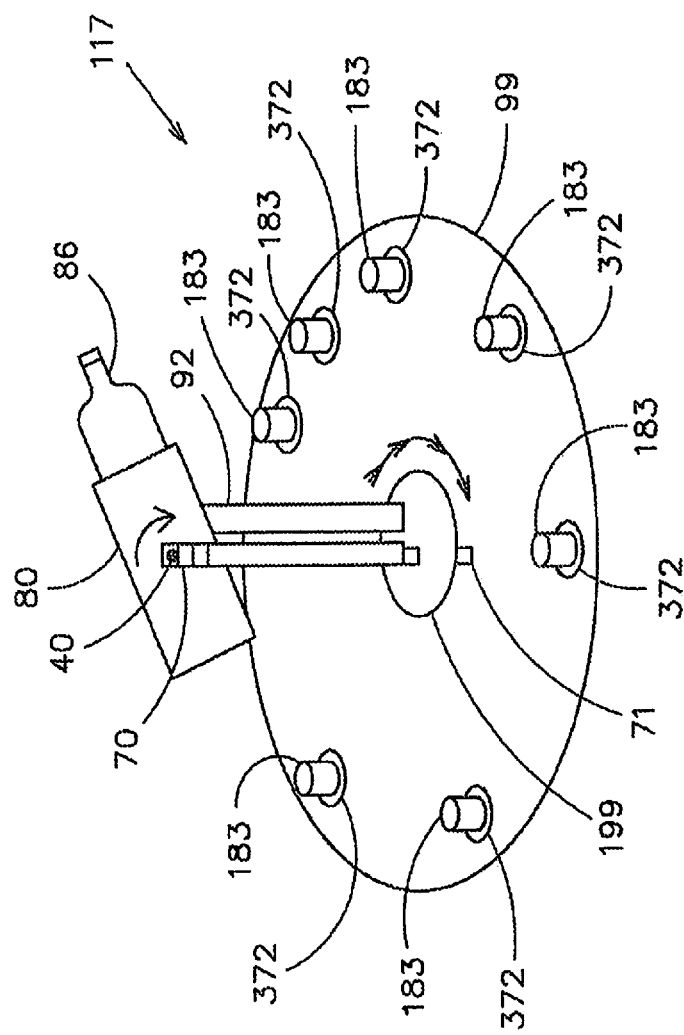
FIG. 19 is a isometric view of another embodiment of the apparatus that can pour the liquid into multiple glasses.

FIG. 19 illustrates another embodiment 117 which provides for filling multiple glasses 183. The container 80 is mounted on vertical rods 92 as described earlier but the vertical rods 92 are mounted on a rotating platform 199 installed on a round base 99. The motor 71 rotates the rotating platform 199 to the proper glass position and the motor 70 controls the portion of liquid poured from the bottle 86. With this embodiment, the container 80 does not need to return to the full upright position but to a position where no more liquid would be poured from the bottle 86. This would expedite the filling of multiple glasses. FIG. 19 shows multiple shot glasses 183 on sensor pads 372 which detect the presence of each glass 183. If the glass is not present, the apparatus would move onto the next glass that is present. Also, the platform where the glasses 183 are placed can rotate and the container 80 and vertical rods 92 are fixed in the round base 99.

According to another embodiment, a beverage pouring apparatus comprises (1) means for accepting and holding a bottle containing a beverage and (2) means for at least semi-automatically moving the bottle in an angular movement from a first position to a second position, wherein the first position is a position maintaining the beverage within the bottle, and the second position is a pouring position to cause a portion of the beverage to pour into a serving receptacle.

The means for accepting and holding a bottle containing a beverage may be any one of the containers 80, 81, 89, 180, 181, 280, 281, or 580. Alternatively, the means for accepting and holding a bottle containing a beverage may be any one the frames 480 or 680. Alternatively, the means for accepting and holding a bottle containing a beverage may be any equivalent of the foregoing.

The means for at least semi-automatically moving the bottle may be any one of these types of motors 70, 170, 175, or 177. Alternatively, other types of motors that not electrical can be used.

CONCLUSION

The terms and descriptions used above are set forth by way of illustration only and are not meant as limitations. Those skilled in the art will recognize that many variations, enhancements and modifications of the concepts described herein are possible without departing from the underlying principles of the invention. For example, the subject matter disclosed in any sentence or paragraph herein can be combined with the subject matter of one

The invention claimed is:

1. A beverage dispenser comprising:
a bottle holder configured to hold a multi-serving bottle of a liquid beverage;
a motor connected to the bottle holder to cause the bottle holder to tilt; and
a controller configured to automatically control the bottle holder via the motor to experience multiple tilting movements, including multiple tilting movements via a cycle, each cycle of which causes the bottle to tilt by a predetermined angular for a predetermined time to bring the bottle into a pouring position to dispense a predetermined quantity, a single serving, of the liquid beverage by gravity from the bottle into a serving receptacle and to return the bottle to an upright position.

2. A beverage dispenser according to claim 1, wherein the liquid beverage is wine, and the serving receptacle is a wine glass.

3. A beverage dispenser according to claim 1, wherein the liquid beverage is liquor.

4. A beverage dispenser according to claim 3, wherein the serving receptacle is a shot glass.

5. A beverage dispenser according to claim 1, wherein the bottle holder is a container.

6. A beverage dispenser according to claim 5, wherein the container is insulated.

7. A beverage dispenser according to claim 1, wherein the bottle holder is a wired cage.

8. A beverage dispenser according to claim 1, wherein the motor is an electric motor.

9. A beverage dispenser according to claim 1, wherein the controller is selected from the group consisting of a computer, a microcontroller, and control circuitry.

10. A beverage dispenser according to claim 1, wherein the serving of the liquid is an amount of the liquid to fill the serving receptacle to a designated level.

11. A beverage dispenser according to claim 1, further comprising:
a sensor configured to detect presence of the receptacle in a position to accept the beverage poured from the bottle; and
wherein the controller is further programmed to dispense a serving of the beverage from the bottle into the serving receptacle when the receptacle is detected via the sensor.

12. A beverage dispenser according to claim 11, wherein the sensor is selected from a group consisting of a weight sensor, a switch, a photo detector sensor, a motion sensor, a distance sensor, and a force sensor.

13. A beverage dispenser according to claim 1, further comprising:
a wireless receiver configured to accept signals from a remote device, and wherein the controller is connected to the wireless receiver to accept a command from the remote device.

14. A beverage dispenser according to claim 13, wherein the remote device is selected from a group consisting of a handheld computer, a tablet, or a smart phone.

15. A beverage dispenser according to claim 14, wherein the command is a command to dispense a serving of the beverage into the serving receptacle.

16. A beverage dispenser according to claim 1, further comprising a temperature sensor configured to monitor the temperature of the bottle.

17. A beverage dispenser according to claim 1, further comprising:
a movable platform having a plurality of positions for a respective plurality of serving receptacles; and
a motor connected to the movable platform and configured to move the movable platform to position each of the plurality of serving receptacles into a position to accept a serving of the beverage poured from the bottle, and
wherein the controller is connected to the motor and further configured to move the movable platform to position each of the plurality of serving receptacles into a position to accept a serving of the beverage poured from the bottle.

18. A beverage dispenser according to claim 17, wherein the movable platform is a turntable.

19. A method comprising:
mechanically accepting and holding a bottle containing a beverage; and
automatically controlling a motor for moving the bottle in an angular movement from a first position to a second position, wherein the first position is a position maintaining the beverage within the bottle, and the second position is a pouring position to cause a predetermined quantity, a serving, of the beverage by gravity to pour into a serving receptacle in which the predetermined quantity is determined by a preprogrammed angular movements over time.

20. A beverage pouring apparatus comprising:
means for accepting and holding a multi-serving bottle containing a beverage; and
means for controlling a motor automatically to move the bottle in an angular movement from a first position to a second position, wherein the first position is a position maintaining the beverage within the bottle, and the second position is a pouring position to cause a predetermined quantity, a serving, of the beverage by gravity to pour into a serving receptacle in which the predetermined quantity is determined by a preprogrammed angular movements over time.

* * * * *